(12) United States Patent
Tsujimura et al.

(10) Patent No.: US 8,681,207 B2
(45) Date of Patent: Mar. 25, 2014

(54) IMAGE PICKUP DEVICE AND ENDOSCOPE PROVIDED WITH IMAGE PICKUP DEVICE

(75) Inventors: Kouji Tsujimura, Kurokawa-gun (JP); Hisashi Suzuki, Kurokawa-gun (JP)

(73) Assignee: FUJIFILM Corporation, Tokyo (JP)

( * ) Notice: Subject to any disclaimer, the term of this patent is extended or adjusted under 35 U.S.C. 154(b) by 1026 days.

(21) Appl. No.: 12/676,668

(22) PCT Filed: Sep. 26, 2008

(86) PCT No.: PCT/JP2008/067984
§ 371 (c)(1),
(2), (4) Date: Mar. 5, 2010

(87) PCT Pub. No.: WO2009/041723
PCT Pub. Date: Apr. 2, 2009

(65) Prior Publication Data
US 2010/0231702 A1    Sep. 16, 2010

(30) Foreign Application Priority Data

Sep. 28, 2007    (JP) .................................. 2007-256701

(51) Int. Cl.
*H04N 7/18*    (2006.01)
*H04N 9/47*    (2006.01)

(52) U.S. Cl.
USPC .......................................................... 348/65

(58) Field of Classification Search
USPC ........................ 348/61, 65; 257/731; 600/459
See application file for complete search history.

(56) References Cited

U.S. PATENT DOCUMENTS

| 5,220,198 A * | 6/1993 | Tsuji ............................. 257/731 |
| 2006/0025691 A1* | 2/2006 | Tanaka et al. ................. 600/459 |

FOREIGN PATENT DOCUMENTS

| JP | 04-034873 A | 2/1992 | |
| JP | 05-115436 A | 5/1993 | |
| JP | 07-264454 A | 10/1995 | |
| JP | 2000-091009 A | 3/2000 | |
| JP | 2000091009 A * | 3/2000 | ............. H01R 12/32 |
| JP | 2001-275022 A | 10/2001 | |
| JP | 2001275022 A * | 10/2001 | ............. H04N 5/225 |

OTHER PUBLICATIONS

IPER corresponding to PCT/JP2008067984, dated Apr. 8, 2010.

* cited by examiner

*Primary Examiner* — Allen Wong
(74) *Attorney, Agent, or Firm* — Sughrue Mion, PLLC

(57) ABSTRACT

An image pickup device mounted at a distal end portion of an endoscope is provided that can make joining work more efficient and simplified, improve maintenance performance and reduce the size and diameter. A distal end portion 44 of an endoscope is provided with an objective optical system 54, a prism 62 continuing to the objective optical system 54, a solid-state image pickup element 66 receiving observation light through the prism 62, a circuit board 68 electrically connected to the solid-state image pickup element 66, and a signal cable having a plurality of cable cores 78, and the circuit board 68 and the signal cable are electrically connected through a connection portion 74 and a joining member 76.

17 Claims, 13 Drawing Sheets

IMAGE PICKUP DEVICE AND ENDOSCOPE PROVIDED WITH IMAGE PICKUP DEVICE

TECHNICAL FIELD

The present invention relates to an image pickup device and an endoscope provided with the image pickup device.

BACKGROUND ART

Electronic endoscope devices for a living body to be inserted into a body cavity for internal observation have been developed. In general, such electronic endoscope device is provided with a lens, a solid-state image pickup element (CCD) and the like at a distal end of its insertion portion. An observed image is formed by the solid-state image pickup element through the lens and photoelectrically converted. An electric signal indicating the photoelectrically converted observed image is processed as appropriate by a processor and outputted to a monitor TV, which displays the observed image.

Size reduction is sought after for from various reasons image pickup devices in which a lens and a solid-state image pickup element are provided at a distal end of an electronic endoscope.

Regarding a structure to reduce the size of an image pickup device mounted at the distal end of an endoscope, Japanese Patent Application Laid-Open No. 5-115436 discloses size reduction of the image pickup device by mounting parts on a flexible board connected to the solid-state image pickup element and by bending the flexible board in a cylindrical shape so as to enlarge a mounting area.

DISCLOSURE OF THE INVENTION

However, the image pickup device described in Japanese Patent Application Laid-Open No. 5-115436 has a structure that a signal cable can not be connected till a peripheral circuit IC, a capacitor, and a resistor are mounted on the flexible board and the board is bent and mounted on the solid-state image pickup element. Thus, soldering work should be carried out while rigidity of the flexible board is lowered.

Particularly, in soldering for electrically joining the circuit board and the signal cable, skills of skilled workers are relied upon with the trend of reduction in diameter and size of the image pickup device. Also, a yield ratio of this joining work process is not particularly good. The conventional connecting method between the circuit board and the signal cable has been an obstacle to the size and diameter reduction.

The present invention was made in view of the above circumstances and has an object to provide an image pickup device mounted at a distal end portion of an endoscope, in which joining work can be made more efficient and simplified, maintenance performance is improved, and reduction in size and diameter can be promoted.

In order to achieve the above object, an image pickup device of the present invention comprises a solid-state image pickup element, a circuit board electrically connected to the solid-state image pickup element, and a signal cable having a plurality of cable cores supplying power and a driving signal to the solid-state image pickup element, and the circuit board having a connection terminal at an end connected to the cable cores of the signal cable, and an interval between the connection terminals being wider than a wiring interval on the circuit board. Moreover, a joining member having a wiring pattern electrically connecting the signal cable and the circuit board is further provided, in which the joining member has a plurality of first connection terminals connected to the cable cores of the signal cable and a plurality of second connection terminals connected to the circuit board at both ends of the wiring pattern, and the interval between the first connection terminals is wider than the interval between the second connection terminals.

In the present invention, by making the interval between the terminals connected to the cable cores wider than the interval between the terminals connected to the circuit board, difficulty in the soldering work is eased, and occurrence of short-circuit by solder between the adjacent connection terminals can be prevented.

An image pickup device of the present invention is characterized in that said joining member of the image pickup device in the above invention is formed cylindrically so that a length of an end portion of the joining member where the first connection terminals are formed is longer than the length of an end portion where the second connection terminals are formed, and an outer diameter on the side connected to the signal cable is larger than the outer diameter on the side connected to the circuit board.

By increasing the length of a side of a region where the first connection terminals are formed, soldering work and the like between the cable cores of the signal cable and the first connection terminals is simplified. Also, the cylindrical shape can reduce the size of the image pickup device in the radial direction.

The image pickup device of the present invention is characterized in that in the above invention, the joining member is a flexible member in which a wiring pattern is formed on an insulating film. By making the joining member by a flexible member, machining such as bending is facilitated. By machining and deforming the joining member, freedom of connection between the circuit board and the signal cable can be considerably improved.

The image pickup device of the present invention is characterized in that in the above invention, a connection portion is further provided between the circuit board and the joining member, and the circuit board and the joining member are eclectically connected through the connection portion. By interposing the connection portion between the circuit board and the joining member, freedom of connection between the circuit board and the joining member can be improved. That is, since the connection portion functions as a connector, the circuit board and the joining member can be easily connected.

The image pickup device of the present invention is characterized in that in the above invention, the joining member and the connection portion are positioned and fixed by engaging a groove or a projection formed on the joining member and a projection or a groove formed on the connection portion. By fitting the groove and the projection with each other, the joining member and the connection portion are relatively positioned, and wrong insertion is prevented.

The image pickup device of the present invention is characterized in that in the above invention, the joining member and the connection portion are provided detachably.

By making them detachable, the signal cable, the circuit board and the solid-state image pickup element can be subjected to electric performance inspection individually. If the signal cable, the circuit board, and the solid-state image pickup element should be comprehensively inspected after the signal cable is connected by solder and the like as before, only the whole evaluation is possible, and guarantee per process is difficult. By making them detachable, the process can be segmented, and quality can be made stable in each process.

The image pickup device of the present invention is characterized in that in the above invention, a pressing member arranged on the side opposite to the connection portion with respect to the joining member is further provided and the joining member is sandwiched between the joining member and the pressing member.

By having a sandwiching structure in which the joining member is sandwiched between the connection portion and the pressing member, connection strength of the joining member and the connection portion can be ensured. Also, since the joining member is held by being sandwiched between the connection portion and the pressing member, electric connection without using solder and the like becomes possible.

The image pickup device of the present invention is characterized in that in the above invention, the joining member is provided with a full-face ground pattern or mesh ground pattern on a face where the wiring pattern is not formed.

The image pickup device of the present invention is characterized in that in the above invention, the joining member has a laminate structure in which a conductor pattern and an insulating film are laminated in plural, and the conductor pattern located in the middle is the full-face ground pattern or mesh ground pattern.

By providing the above-mentioned ground pattern on the joining member, a noise measure is taken, and a signal can be stabilized.

An endoscope of the present invention is characterized by being provided with the above image pickup device.

According to the present invention, joining work of the signal cable and the circuit board can be made more efficient and simplified, the size of the endoscope image pickup device can be reduced, and maintenance performance can be improved.

DESCRIPTION OF SYMBOLS

54 . . . objective optical system, 62 . . . prism, 66 . . . solid-state image pickup element, 68 . . . circuit board, 70 . . . component, 74 . . . connection portion, 76 . . . joining member, 78 . . . cable core, 80 . . . signal cable, 94 . . . pressing member, 98, 122 . . . key groove, 124 . . . projection portion

BEST MODE FOR CARRYING OUT THE INVENTION

A preferred embodiment of the present invention will be described below referring to the attached drawings. The present invention will be described according to the following preferred embodiment but is capable of changes in many ways without departing from the scope of the present invention, and embodiments other than the preferred embodiment may be used. Therefore, all the changes in the scope of the present invention are included in claims.

[Entire System of Endoscope]

Figure 1:
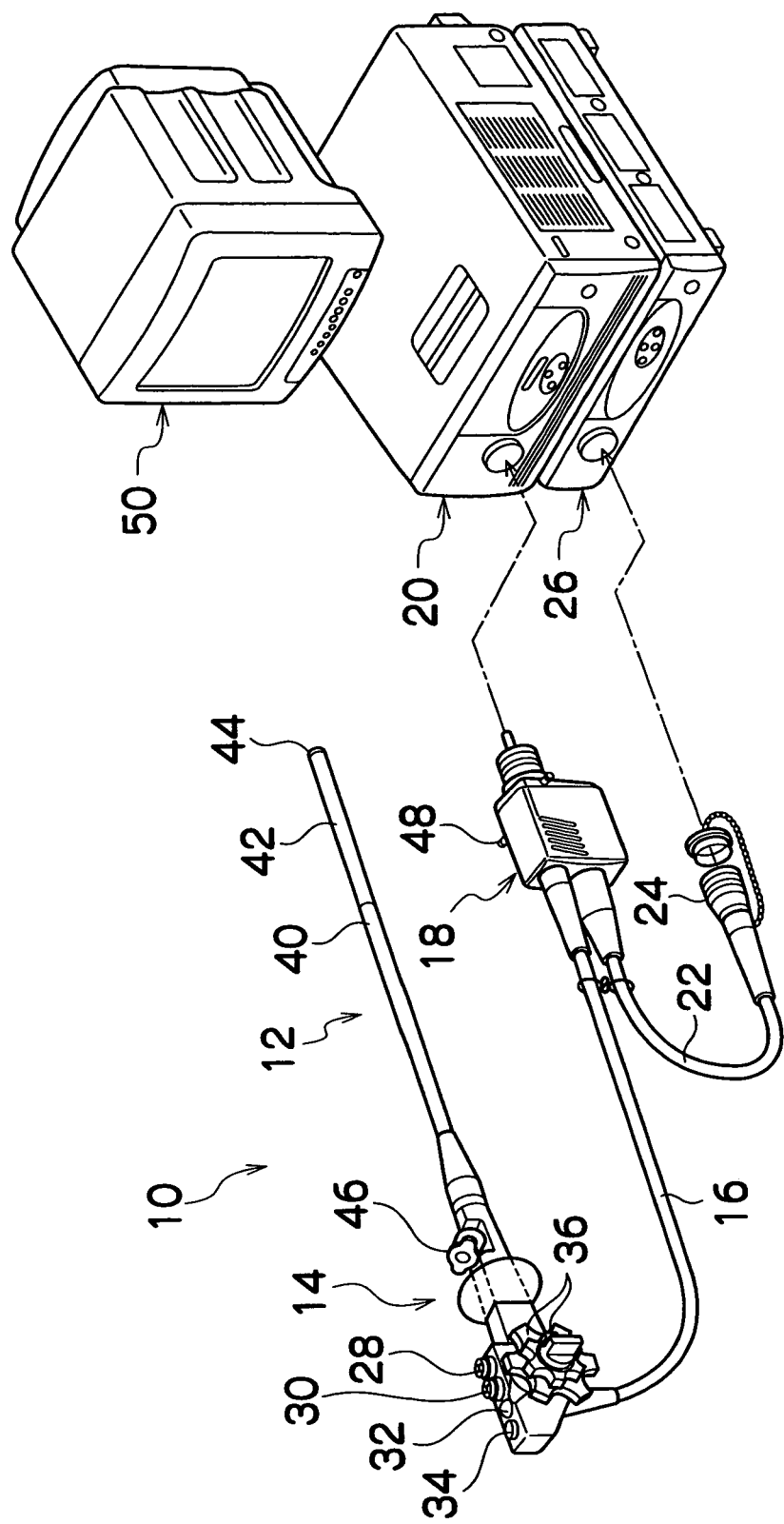
FIG. 1 is a block diagram illustrating an entire system of an endoscope.

FIG. 1 shows entire configuration of a system of an endoscope in which the image pickup device of the present invention is used. As shown in FIG. 1, an endoscope device is provided with an endoscope 10. The endoscope 10 is provided with a hand-side operation portion 14 and an insertion portion 12 provided continuously to the hand-side operation portion 14 and inserted into a body cavity. To the hand-side operation portion 14, a universal cable 16 is connected, and at a distal end of the universal cable 16, an LG connector 18 is provided. The LG connector 18 is detachably connected to a light source device 20. Through the LG connector 18, illumination light is sent to an illumination optical system (not shown). Also, to the LG connector 18, an electric connector 24 is connected through a cable 22. The electric connector 24 is detachably connected to a processor 26.

At the hand-side operation portion 14, an air/water feed button 28, a suction button 30, a shutter button 32, a function switch button 34, and a pair of angle knobs 36, 36 are provided.

The insertion portion 12 is constituted by a flexible portion 40, a bending portion 42, and a distal end portion 44 in order from the hand-side operation portion 14 side. The bending portion 42 is remotely bent and operated by rotating the angle knobs 36, 36 of the hand-side operation portion 14. Thereby, the distal end portion 44 can be directed to a desired direction.

[Distal End Portion of the Endoscope]

Figure 2:
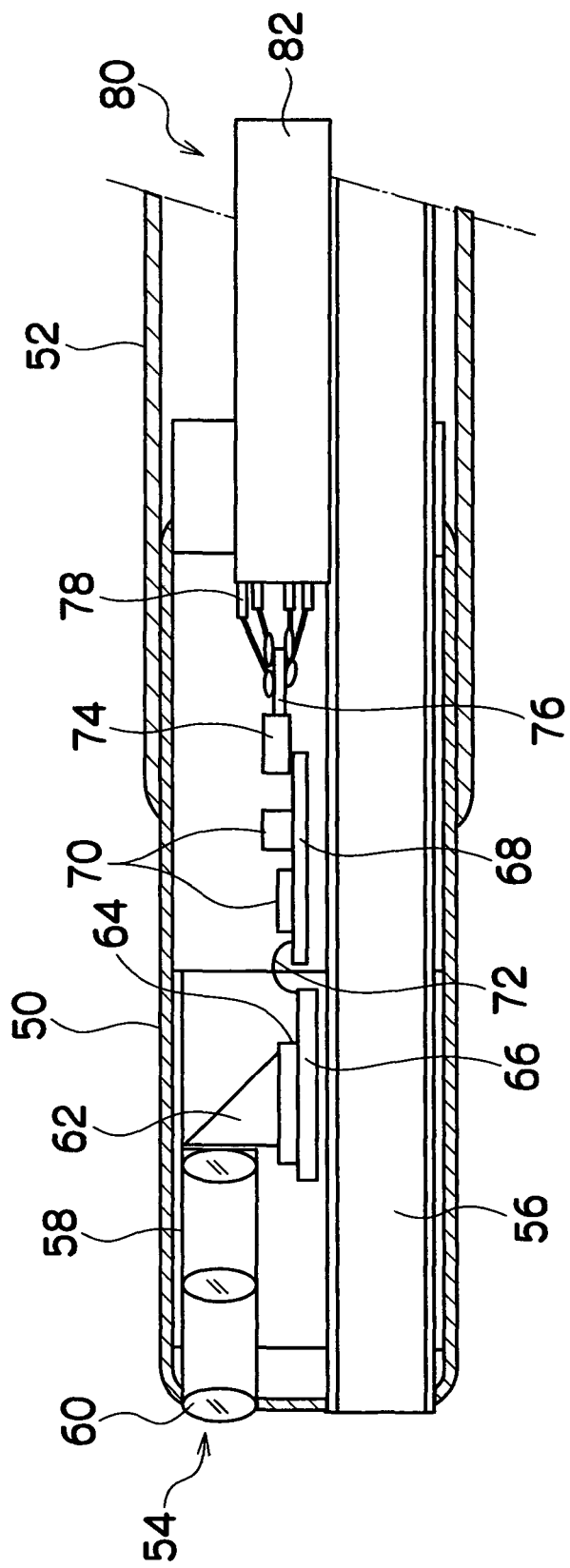
FIG. 2 is a sectional view illustrating a distal end portion of the endoscope.

Next, the distal end portion 44 of the endoscope will be described referring to FIG. 2. The distal end portion 44 is provided with a metal cylindrical fitting 50 which can not be bent. One end portion of the cylindrical fitting 50 is covered by a cover layer 52 made of synthetic resin, and a base end portion of the cover layer 52 is connected to an endoscope hand-held operation portion, not shown.

In the cylindrical fitting 50, an objective optical system 54, a forceps port 56, a light guide (not shown), an air/water feed channel (not shown) and the like are provided.

The objective optical system 54 is constituted by a plurality of lenses 60 arranged inside a lens barrel 56. Behind the objective optical system 54, a prism 62 is provided, and the prism 62 changes the direction of incident light into the objective optical system 54 by 90°. Below the prism 62, a solid-state image pickup element 66 provided with a cover glass 64 is provided. An observed image (optical signal) taken in by an observation optical system is formed at a light receiving portion of the solid-state image pickup element 66 through the lens 60 and the cover glass 64, and the optical signal is converted into an electric signal.

Behind the solid-state image pickup element 66, a circuit board 68 on which a plurality of electronic components 70, 70, . . . such as an IC, a resistor, a capacitor, a transistor and the like are mounted is provided. The circuit board 68 and the solid-state image pickup element 66 are electrically connected by a lead wire 72 and the like.

At the rear end of the cylindrical fitting 50, a signal cable 80 is provided, and the signal cable 80 is constituted by a plurality of cable cores 78, 78, . . . and a sheath material 82 covering the cable cores. The signal cable 80 supplies power for driving the solid-state image pickup element 66 and components 70 through the cable cores 78, 78 . . . and transmits an electric signal photoelectrically converted at the solid-state image pickup element 66 to a processor portion 26 in FIG. 1.

The plurality of cable cores 78, 78 . . . of the signal cable 80 and the circuit board 68 are electrically connected from the cable core 78 side through a joining member 76 and a connection portion 74.

Next, a method of connecting the signal cable 80 and the circuit board 68 using the joining member 76 and the connection portion 74 will be described.

Figure 3:
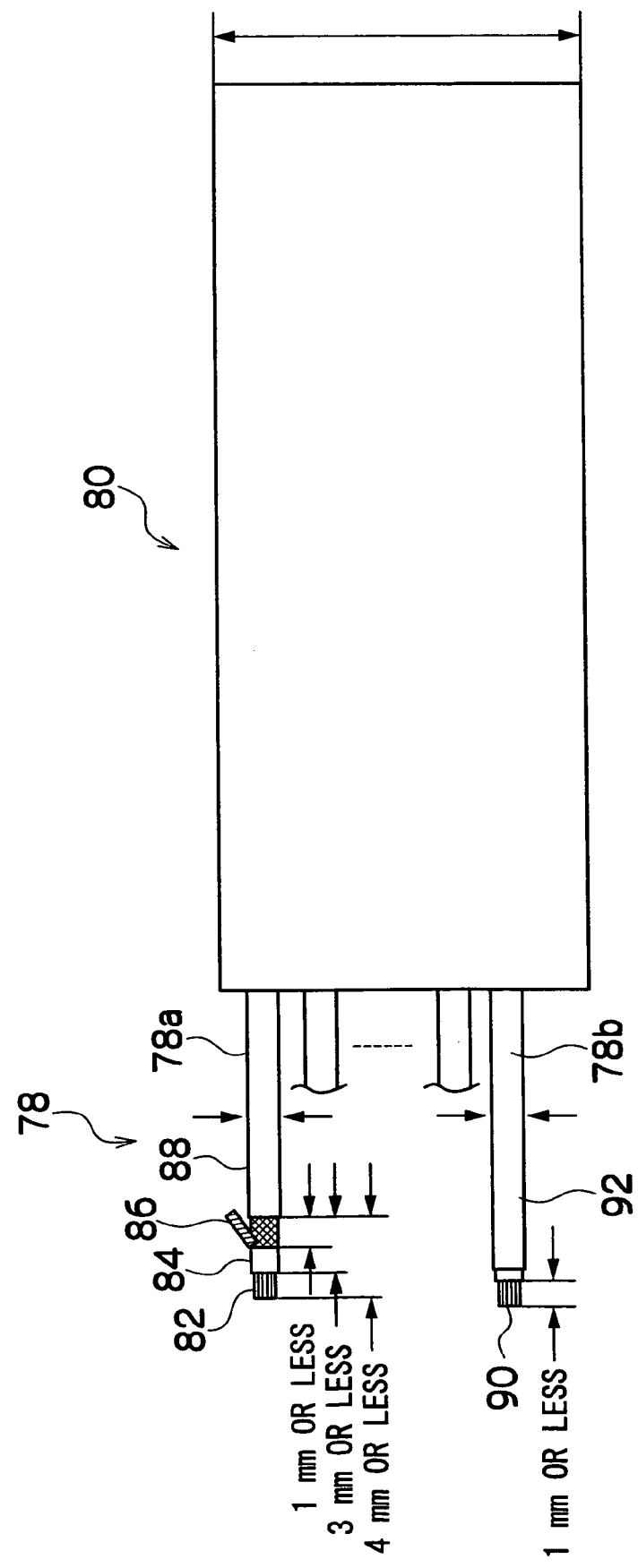
FIG. 3 is a configuration diagram of a signal cable.

FIG. 3 shows the signal cable used in the image pickup device before connection. The signal cable 80 used in an endoscope is provided with the plurality of cable cores 78. Not all of the plurality of cable cores 78 are the same but they have at least two types of structure. One of them is a coaxial cable 78a, while the other is a single-wire cable 78b. The coaxial cable 78a is constituted by a conductor 82 made of silver-plated copper alloy with an outer diameter of Φ0.01 to 0.1 mm, for example, a conductor coating 84 coating the conductor, a braided shield 86 formed so as to cover the conductor coating 84, and an outer-peripheral coating 88 covering the braided shield 86. The outer diameter of the coaxial cable 78a constituted as above is approximately Φ0.15 to 0.5 mm, for example. With regard to processing of a terminal of the coaxial cable 78a, a length from the outer-peripheral coating 88 to the distal end of the conductor 86 is 4 mm or less, a length from the outer-peripheral coating 88 to the distal end of the conductor coating 84 is 3 mm or less, and a length from the outer-peripheral coating 88 to the distal end of the braided shield 86 is 1 mm or less.

On the other hand, the single-wire cable 78b is constituted by a conductor 90 made from silver-plated copper alloy and having an outer diameter of Φ0.01 to 0.1 mm, for example, and a conductor coating 92 coating the conductor. The outer diameter of the single-wire cable 78b constituted as above is approximately Φ0.15 to 0.5 mm, for example. With regard to the processing of the terminal of the single-wire cable 78b, a length from the outer-peripheral coating 92 to the conductor 90 is 1 mm or less.

The signal cable 80 is provided with 8 to 20 pieces of cable cores, combining the coaxial cable 78a and the single-wire cable 78b in general. The outer diameter of the signal cable 80 is Φ0.8 to 2.5 mm, for example. Thicknesses, materials and the number of the coaxial cable 78a and the single-wire cable 78b are determined as appropriate according to the type of the endoscope.

First Embodiment

Figure 4:
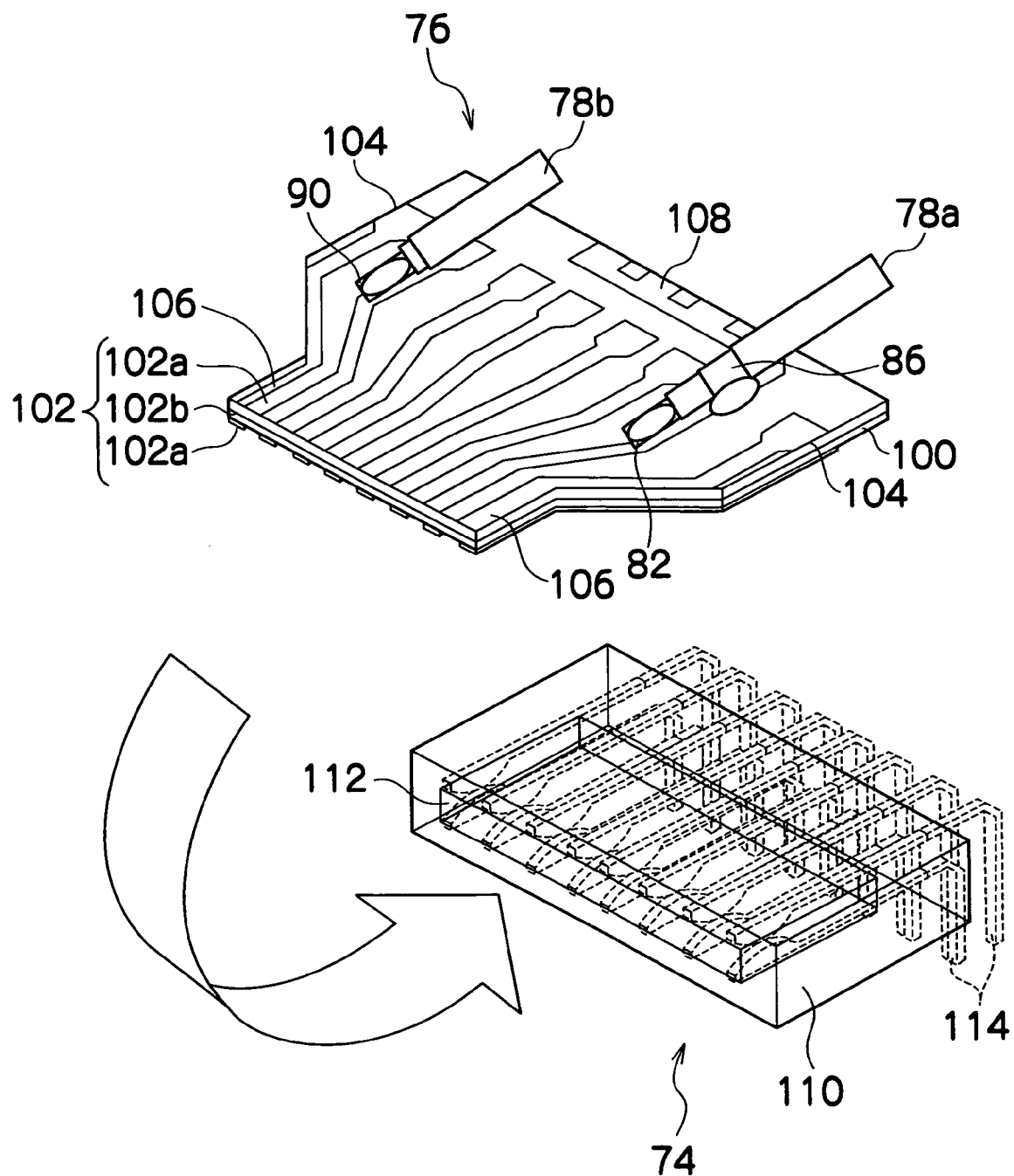
FIG. 4 is a diagram for explaining connection between a joining member and a connection portion according to a first embodiment.
Figure 5:
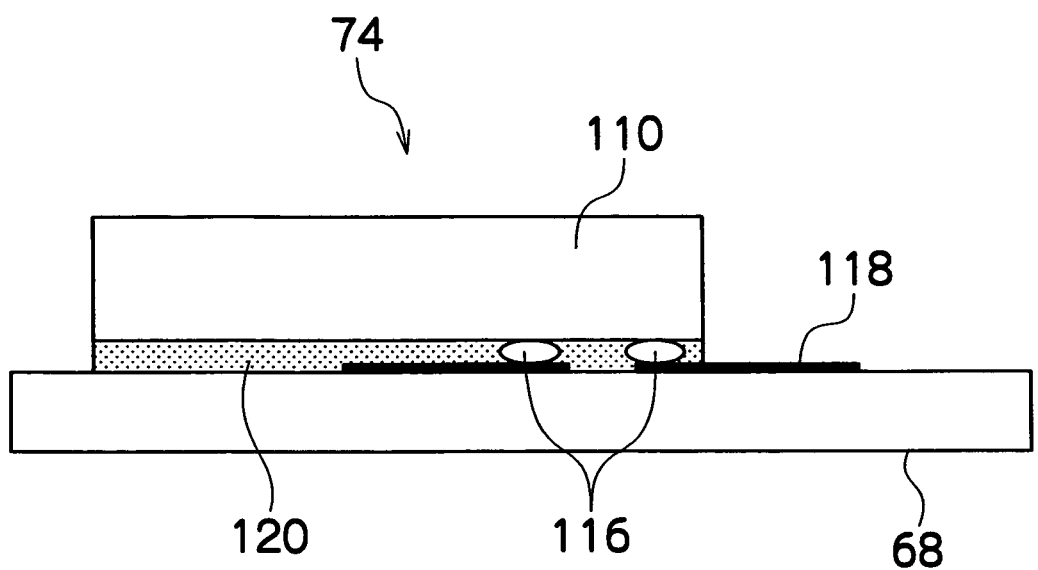
FIG. 5 is a diagram for explaining connection between the connection portion and a circuit board according to the first embodiment.

A first embodiment will be described referring to FIGS. 4 to 6. As shown in FIG. 4, the joining member 76 is mainly constituted by an insulating film 100 of polyimide, PET or the like and a conductor pattern 102 made of metal in which copper is gold-plated, provided on the insulating film 100. In this embodiment, the joining member 76 is in a laminate structure in which a plurality of the insulating films 100 and the conductor patterns 102 are laminated. The joining member 76 has a film thickness of 20 to 100 μm, for example, and has flexibility.

The conductor pattern 102 on a surface layer of the insulating film 100 functions as a wiring pattern 102a electrically connecting the signal cable and the circuit board. In the joining member 76 shown in FIG. 4, the wiring pattern 102a has the wiring pattern 102a formed both on front and back faces. The wiring pattern 102a is formed with a width of 25 to 300 μm, for example.

The wiring pattern 102a is provided with a first connection terminal 104 and a second connection terminal 106 at both ends. The first connection terminal 104 is formed by increasing the width of the wiring pattern 102a so that electric connection with the plurality of cable cores of the signal cable is realized. On the other hand, the second connection terminal 106 is formed with the same thickness as the wiring pattern 102a.

In the present invention, a region of the joining member 76 where the first connection terminals 104 are formed is formed wider than a region where the second connection terminals 106 are formed. The both end portions of the joining member 76 is substantially straight. By making the region where the first connection terminals 104 are formed wider, an interval (pitch) between the first connection terminals 104 can be made wider than the interval (pitch) between the second connection terminals 106.

By widening the width between the first connection terminals 104 to be connected to the cable wires, difficulty in soldering work is eased. Also, occurrence of short-circuit by outflow of solder between the adjacent first connection terminals 104 can be prevented. The interval between the first connection terminals 104 is 200 to 400 μm, for example, while the interval between the second connection terminals 106 is 25 to 400 μm, for example. Particularly, facilitation of the soldering work and prevention of short-circuit involved in soldering of a super fine cable core and a connection terminal used in an endoscope are extremely important in improving the yield ratio.

The first connection terminal 104 has two types of shape according to the type of cable core to be connected. With regard to the first connection terminal 104 to be connected to the single-wire cable 78b, only a portion to be connected to the conductor 90 is formed at an end portion of the wiring pattern 102a. On the other hand, the first connection terminal 104 to be connected to the coaxial cable 78a is provided with a ground terminal 108 for shield to be connected to the braided shield 86 of the coaxial cable in addition to the portion to be connected to the conductor 82.

Alternatively, the conductor pattern 102 located at an intermediate position of the laminate structure for a measure against noise may be a ground pattern 102b of a full-face ground pattern, mesh ground or the like. The ground pattern 102b and the ground terminal 108 are electrically connected to have an equal potential.

On a portion where the second connection terminal 106 is formed, the insulating film 100 is laminated and formed thick in order to increase joining strength.

The connection portion 74 is provided with a housing 110 manufactured from a synthetic resin and the like, an insertion port 112 formed at the housing 110 for accommodating the joining member 76, and a plurality of pins 114 held by the housing 110 and partially protruding from the housing 110.

At the insertion port 112, the pins 114 are vertically aligned along the width direction of the housing 110, by which the pins 114 can be electrically connected to the wiring pattern 102a formed on both faces of the joining member 76. Since the connection structure between the pins 114 and the second connection terminals 106 is realized by sandwiching the joining member 76 by the vertically aligned pins 114, it makes a detachable structure. With this structure, time for failure analysis, repair can be reduced.

The portion of the pin 114 protruding from the housing 110 is bent downward by 90 degrees. The pins 114 aligned on an upper side are bent at a position far from the housing 110 rather than the pins 114 aligned on a lower side so that the vertically aligned pins 114 do not overlap each other. The pins 114 are electrically connected to the circuit board, and the signal cable and the circuit board are electrically connected through the joining member 76 and the connection portion 74.

In this embodiment, a method of connecting to the circuit board using the pins 114 will be disclosed. As shown in FIG. 5, without having the pins 114 protruded from the housing 110 on the side face, the pins 114 are bent in a direction of a bottom face and a bump 116 may be provided to be electrically connected to the pins 114 on the bottom face. Through this bump 116, the pattern 118 of the circuit board 68 and the connection portion 74 can be electrically connected. A gap between the housing 110 and the circuit board 68 is filled with a resin 120 and the like. Alternatively, the second connection terminal 106 and the circuit board can be directly connected not through the connection portion 74 by providing an ACF, not shown, or a bump at the second connection terminal 106 of the joining member 76.

Figure 6:
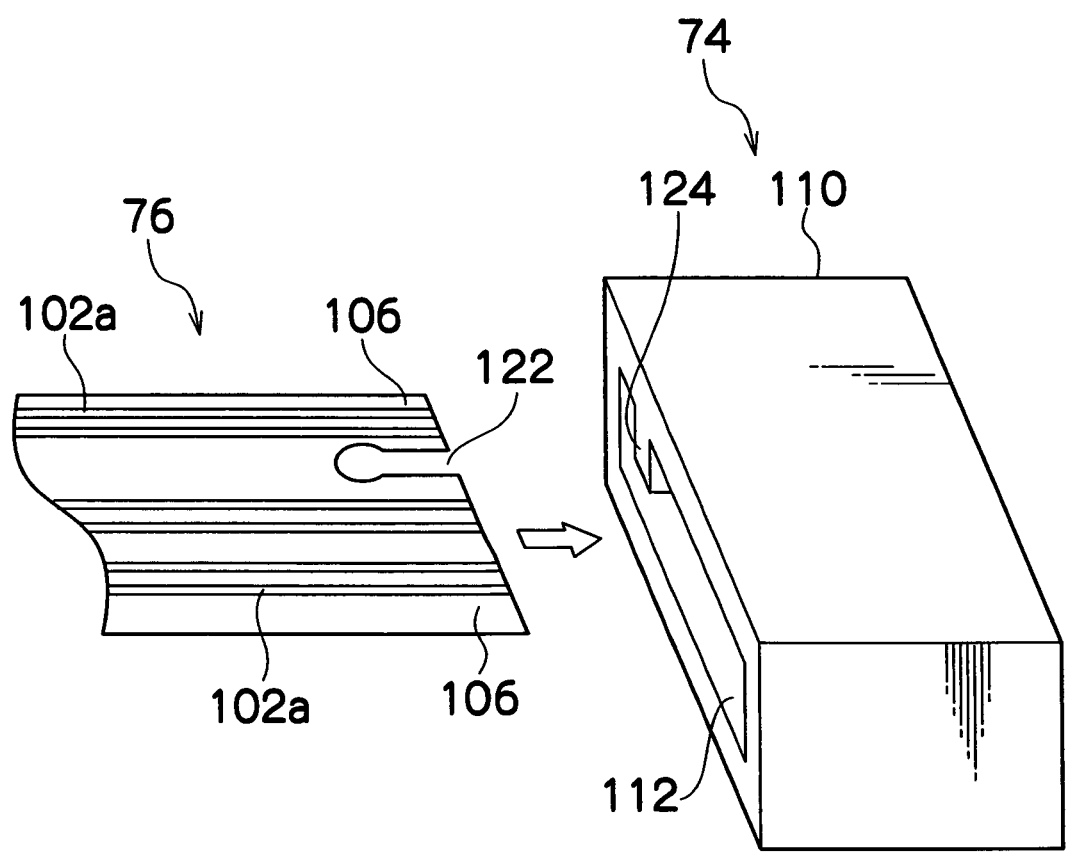
FIG. 6 is a diagram for explaining connection between the joining member and the connection portion according to the first embodiment.

As shown in FIG. 6, in a region of the joining member 76 where the second connection terminal 106 is formed, a key groove 122 for positioning is provided, and a projection portion 124 is provided on the connection portion 74 at a position corresponding to the key groove 122. The key groove 122 is provided at a position offset from the center of the joining member 76, and similarly, the projection portion 124 is provided at a position offset from the center of the connection portion 74. By fitting the key groove 122 and the projection portion 124 with each other, the joining member 76 is positioned at the connection portion 74, by which wrong insertion is prevented.

In this embodiment, the joining member 76 and the circuit board 68 are described as separate bodies. However, in order to reduce the number of components, the circuit board 68 and the joining member 76 can be formed integrally. A signal cable is directly connected electrically to the integrally formed joining member 76.

Second Embodiment

A second embodiment of the present invention will be described referring to FIGS. 7 to 9. The same reference numerals are given to configuration similar to that shown in the first embodiment, and description might be omitted.

Figure 7A:
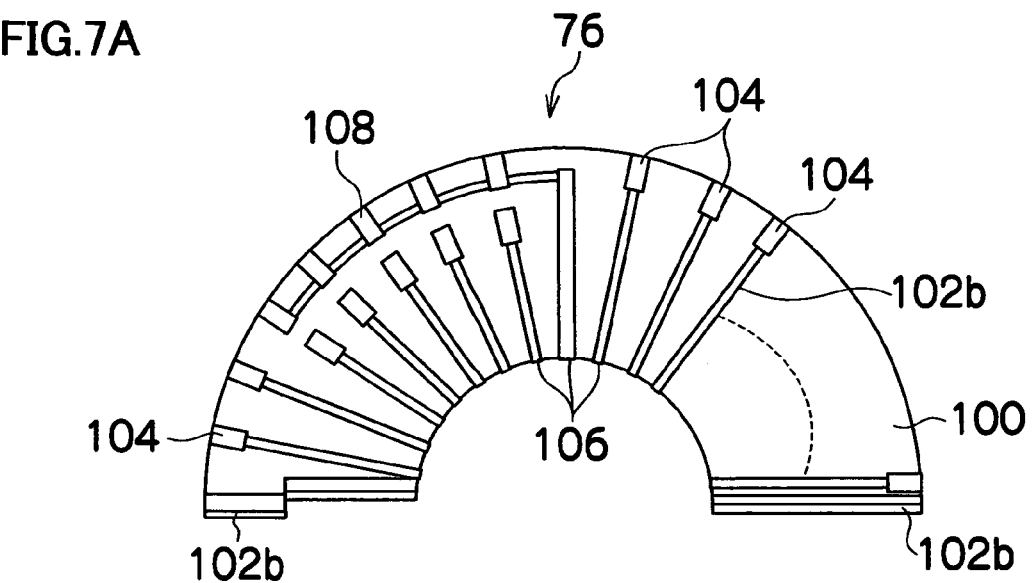
FIGS. 7A to 7C are diagrams for explaining a joining member according to a second embodiment.
Figure 8:
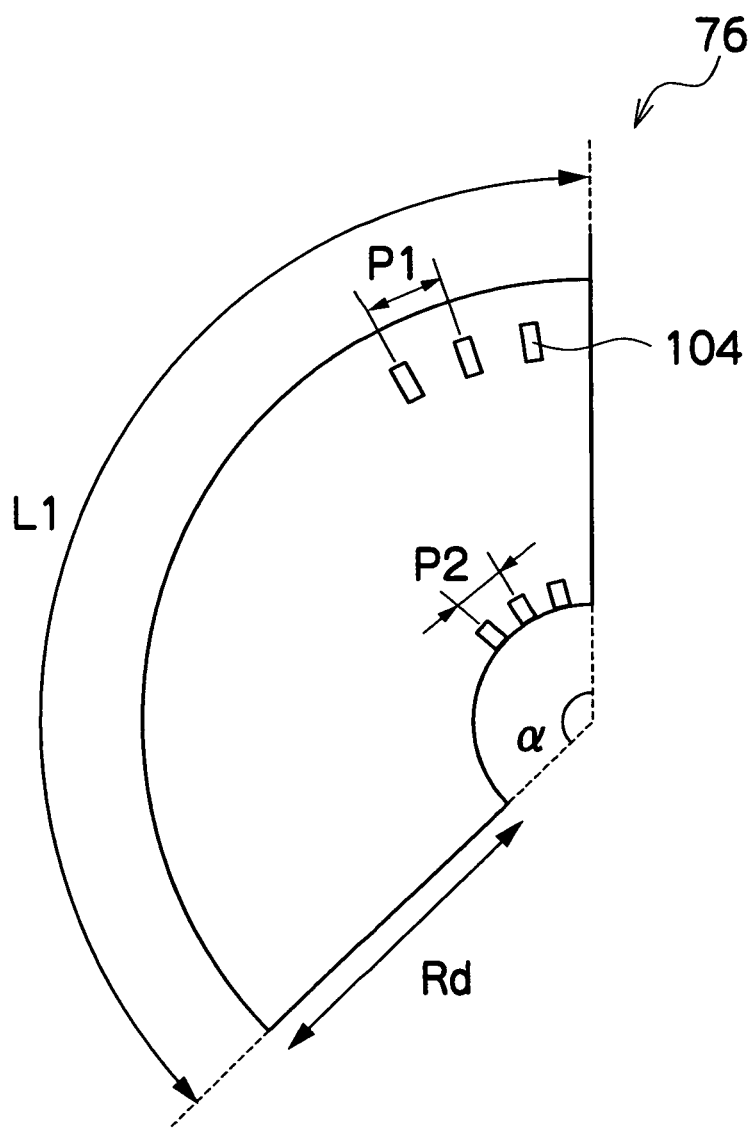
FIG. 8 is a diagram for explaining the joining member according to the second embodiment.

As shown in FIG. 7A, the joining member 76 of this embodiment is constituted by the insulating film 100 and the wiring pattern 102a provided on the insulating film 100 and made of metal in which copper is gold-plated. Unlike the first embodiment, the wiring pattern 102a is formed only on one face of the insulating film 100 in this embodiment.

The wiring pattern 102a is provided with the first connection terminal 104 connected to the signal cable and the second connection terminal 106 at both ends. On a region where the first connection terminal 104 is formed, the ground terminal 108 is provided.

The joining member 76 has a substantially fan shape. The first connection terminals 104 are aligned on an outer peripheral portion of the fan, while the second connection terminals 106 are aligned on an inner peripheral portion of the fan. In this embodiment, too, the interval between the first connection terminals 104 is formed wider than the interval between the second connection terminals 106. Particularly, since the first connection terminals 104 are aligned on the outer periphery side, it becomes possible to further widen the interval between the first connection terminals 104. The soldering work between the cable core 78 and the joining member 76 can be carried out more easily.

On the joining member 76, the key groove 122 for positioning is formed by cutting out a part of the insulating film 100. Also, by forming the ground pattern 102b on the whole surface on the face of the insulating film 100 where the wiring pattern 102a is not formed, a measure against noise is taken. Similarly to the first embodiment, if the joining member 76 is in a laminate structure, the noise measure can be realized by forming the full-face ground pattern, mesh ground or the like at an intermediate position.

Figure 7B:
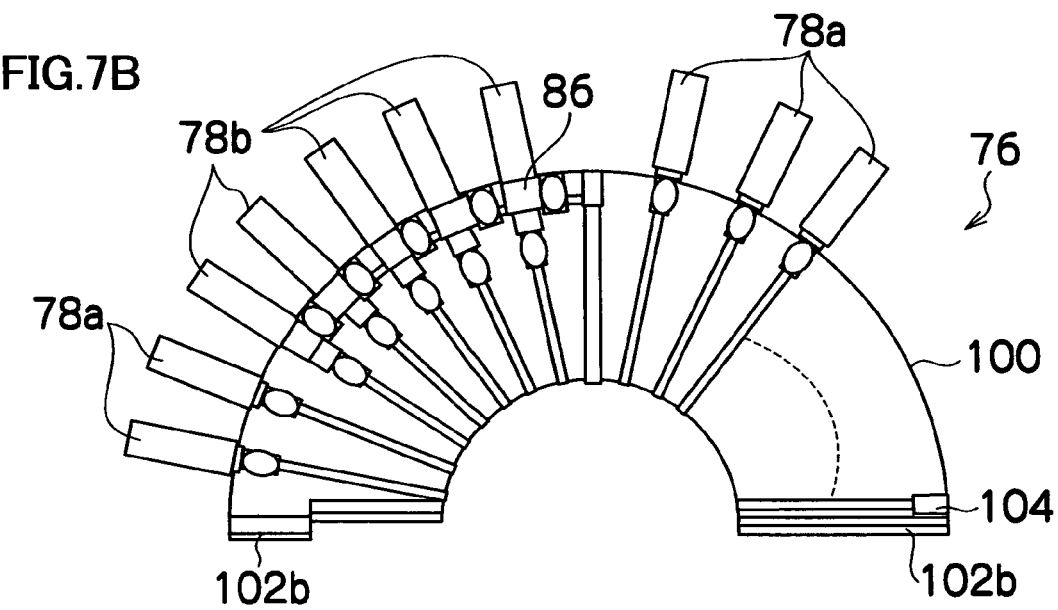

As shown in FIG. 7B, to the first connection terminal 104, the coaxial cable 78a and the single-wire cable 78b are electrically connected. Similarly to the first embodiment, the braided shield 86 is electrically connected to the ground terminal 108. Since the interval between the first connection terminals 104 is formed widely, the soldering work can be carried out easily.

After the connection between the cable core 78 of the signal cable and the first connection terminal 104 is completed, a conduction test is carried out by resistance measurement to check presence of connection failure. If the connection failure is found, treatment such as re-soldering is applied.

Figure 7C:
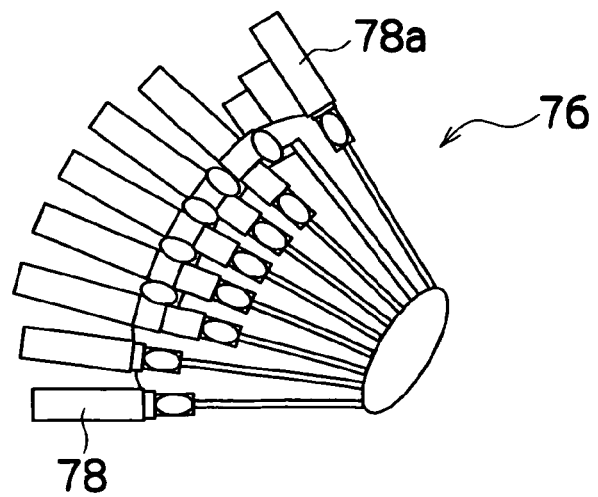

In the case of no connection failure, as shown in FIG. 7C, the insulating film 100 is bent by a jig and the like so as to form the joining member 76 in a truncated cone shape.

In this embodiment, by using the flexible joining member 76, the shape of the joining member is determined after completion of the soldering work. As a result, at a stage where the shape of the joining member is determined, the connection terminals can be arranged so that soldering becomes easy, and the joining member with a small diameter can be obtained by the subsequent molding.

The size of the joining member 76 will be described referring to FIG. 8. As shown in FIG. 8, the joining member 76 has a substantially fan shape. The first connection terminals 104 are provided on an outer peripheral portion. A length of an arc L1 of the outer periphery determines a distance between the pitches of the first connection terminals 104.

Suppose that the outer diameter of the joining member 76 when it is bent is Φ1.5 mm in compliance with the diameter of the signal cable, for example, the length of the arc L1 of the fan-shaped joining member 76 is 4.71 mm. With this length and supposing that the number of the cable cores in the signal cable is 16, a pitch P1 of the first connection terminals 104 is approximately 294 μm, and the solder joining work can be carried out easily. By increasing a substantial length Rd of the joining member 76, a center angle α becomes small.

In the present invention, in correspondence with the pitch of the first connection terminals 104 in demand, the arc length L1, the center angle α, Rd of the joining member 76 can be freely selected, and freedom of connection is improved.

Similarly, suppose that the outer diameter of the joining member 76 when being bent is Φ2.0 mm, the outer periphery is 6.28 mm, and suppose that the number of cable cores is 16, the pitch P1 of the first connection terminals 104 is approximately 392 μm, by which the solder joining work can be carried out more easily.

Suppose that an outer diameter L2 on the second connection end side 106 of the joining member 76 after being bent is Φ0.714 mm, even if the width of the second connection terminal 106 is 70 μm, the interval between the second connection terminals 106 is approximately 90 μm, and the pitch P2 between the second connection terminals 106 is 106 μm. Short-circuit between the second connection terminals 106 can be sufficiently restrained.

The pitch of the second connection end side 106 is determined by the shape and size of the circuit board, connection portion and the like to be electrically connected to the joining member 76.

Figure 9A:
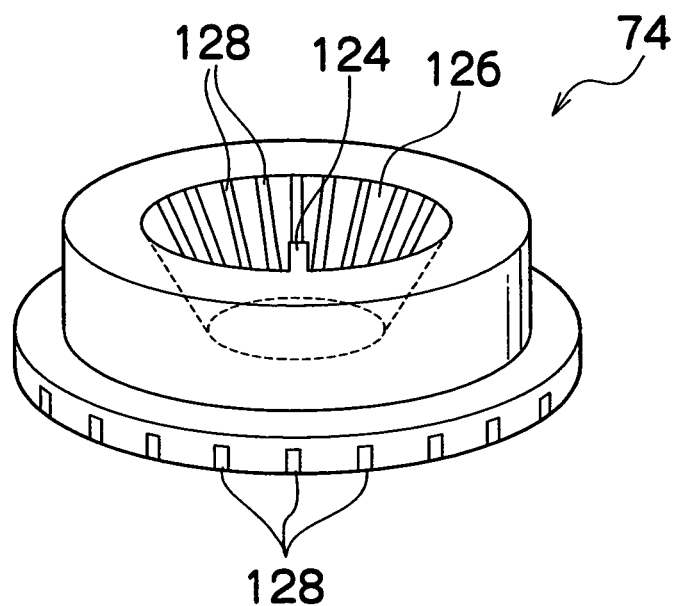
FIGS. 9A and 9B are diagrams for explaining a connection portion according to the second embodiment.

Next, the connection portion 74 to be electrically connected to the joining member 76 of the second embodiment will be described referring to FIG. 8. As shown in FIG. 9A, the connection portion 74 is made of resin or ceramic and has an outer shape of double-stage cylinder. A tapered-shaped through hole 126 is formed in a vertical direction of the connection portion 74. On the tapered face of the through hole 126, an electrode pattern 128 is formed at a position corresponding to a second electrode terminal of the joining member. The electrode pattern 128 is formed by applying gold plating on a copper foil. Also, on the tapered face, the projection portion 124 is formed at a position corresponding to the key groove of the joining member.

Figure 9B:
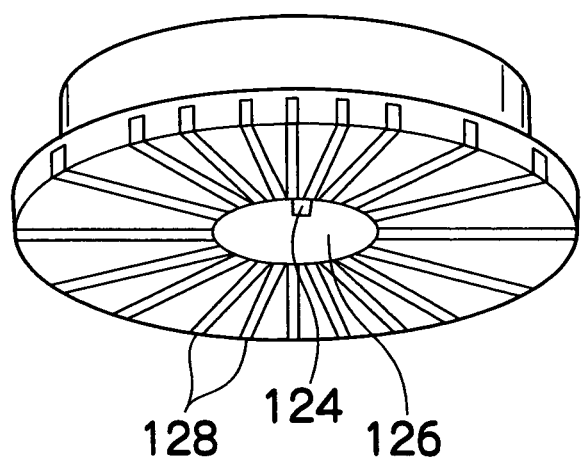

As shown in FIG. 9B, the electrode pattern 128 formed on the tapered face is extended radially from the through hole 126 on the back face side of the connection portion 74 till it reaches the periphery. The back face of the connection portion 74 becomes a connection surface with the circuit board. Connection between the connection portion 74 and the circuit board is realized through the electrode pattern 128 of the connection portion 74 or ACF, bump and the like formed on the pattern of the circuit board. Since the electrode pattern 128 of the connection portion 74 is formed radially from the center, the interval between the electrode patterns 128 is formed widely on the peripheral portion, and the connection portion 74 and the circuit board are electrically connected relatively easily.

Figure 10:
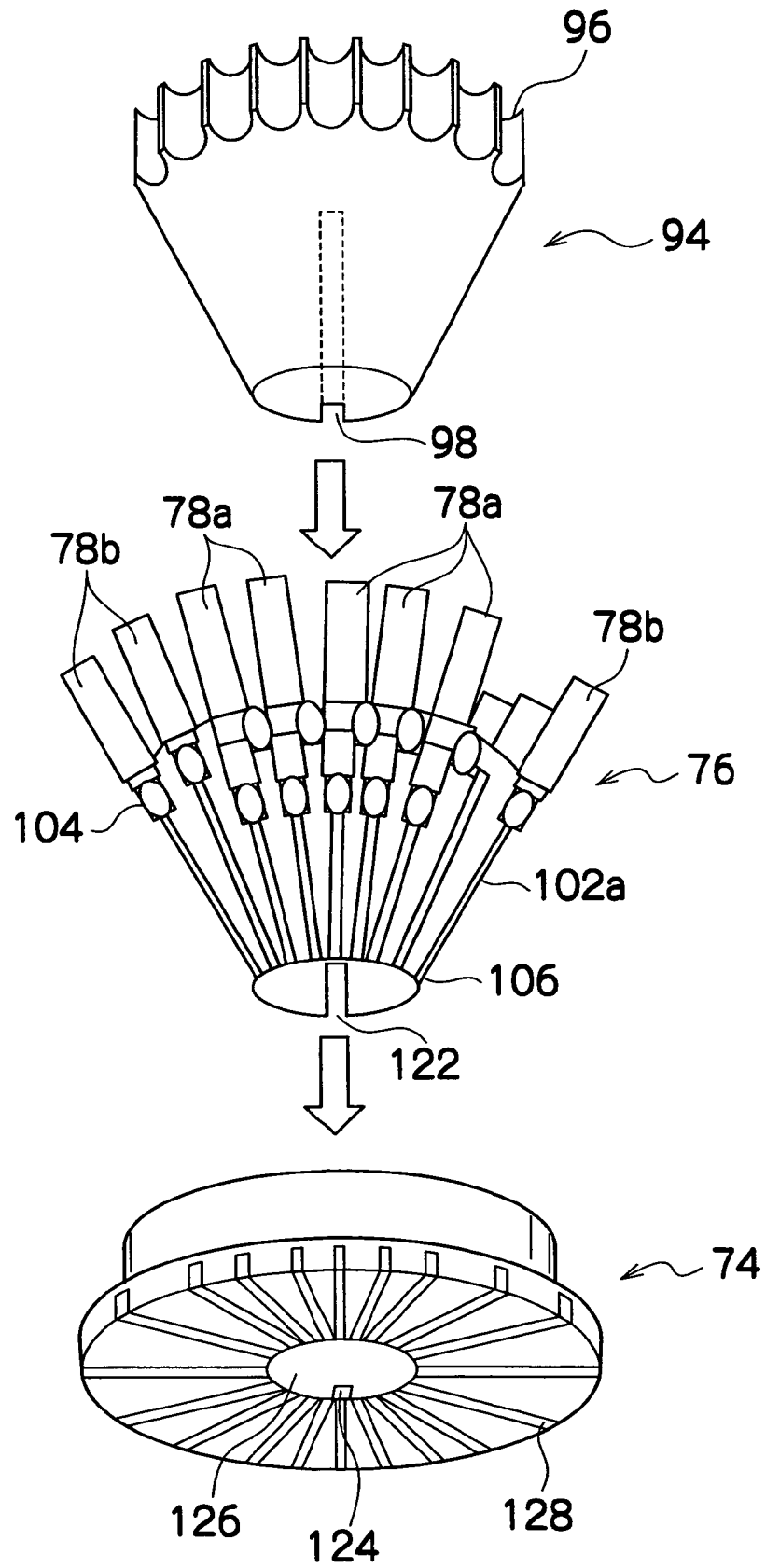
FIG. 10 is a diagram for explaining connection between the joining member and the connection portion according to the second embodiment.

FIG. 10 shows an outline of a method of connecting the joining member 76 and the connection portion 74. Since the shape of the joining member 76 and the shape of the through hole 126 of the connection portion 74 are substantially similar, the joining member 76 is easily inserted into the through hole 126 of the connection portion 74. At the insertion, the key groove 122 of the joining member 76 is fitted with the projection portion 124 of the connection portion 74, and the electrode pattern 128 of the connection portion 74 and the second connection terminal 106 of the joining member 76 are positioned. By using the fitting between the key groove 122 and the projection portion 124, wrong connection between the electrode pattern 128 and the second connection terminal 106 can be prevented.

In order to further ensure connection between the electrode pattern 128 and the second connection terminal 106, a pressing member 94 is inserted to be fitted with the joining member 76 from the side opposite the connection portion 74 with respect to the joining member 76. The pressing member 94 has a substantial truncated cone shape similar to the tapered shapes of the joining member 76 and the through hole 126 of the connection portion 74.

By forming a sandwich structure in which the joining member 76 is sandwiched by the pressing member 94 and the connection portion 74, the electrode pattern 128 and the second connection terminal 106 can be electrically connected not particularly using solder and the like, and the joining member 76 and the connection portion 74 are constructed in a detachable structure. With this structure, time for failure analysis and repair can be reduced.

In the second embodiment, since the joining member 76 has a tapered shape, the size of the connecting member 76 can be made small. By giving an urging force to the pressing member 94, defective contact between the connecting member 76 and the connection portion 74 can be also prevented.

In the pressing member 94, a support groove 96 accommodating cable cores 78 (78a, 78b) and a key groove 98 for positioning are formed.

Assembling is carried out such that 1) the key groove 122 and the projection portion 124 are fitted together and while the joining member 76 and the connection portion 74 are aligned, the joining member 76 is inserted into the connection portion 74; 2) the key groove 98 of the pressing member 94 and the projection portion 124 are fitted together and while the pressing member 94 and the connection portion 74 are aligned, the pressing member 94 is accurately inserted into the joining member 76; 3) the cable core 78 is bonded and fixed to the support groove 96 formed on the pressing member 94; and 4) the connection portion 74 is mounted on the circuit board. However, the order is not limited to the above.

Third Embodiment

A third embodiment of the present invention will be described referring to FIGS. 11 to 13. The same reference numerals are given to configuration similar to that shown in the first and second embodiments, and description might be omitted.

Figure 11A:
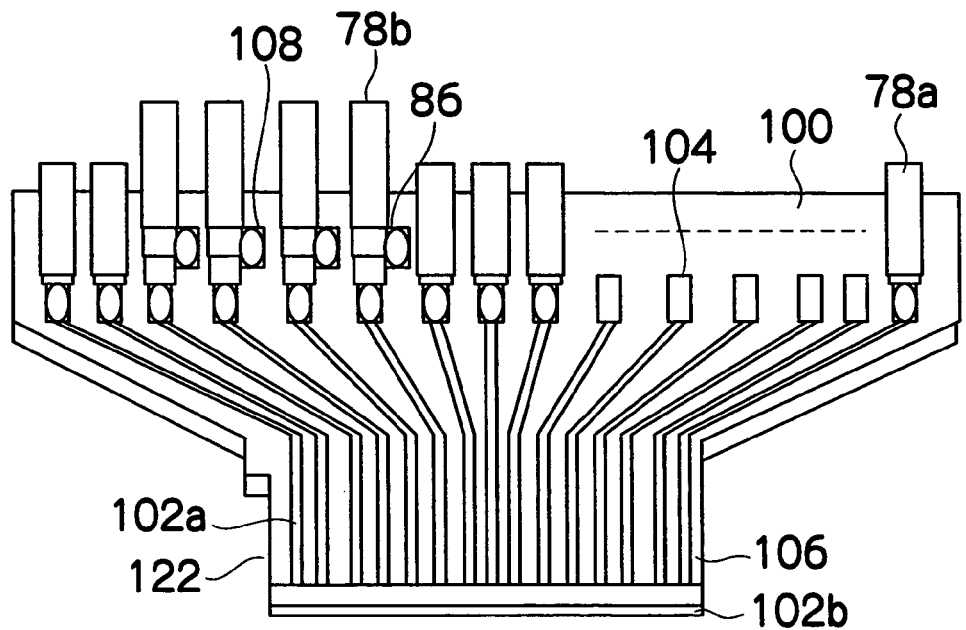
FIGS. 11A and 11B are diagrams for explaining a joining member according to a third embodiment.

As shown in FIG. 11A, the joining member 76 of this embodiment comprises the insulating film 100 and the metal wiring pattern 102a provided on the insulating film 100, in which copper is gold-plated. Similarly to the second embodiment, the wiring pattern 102a is formed only on one face of the insulating film 100 in this embodiment.

The wiring pattern 102a is provided with the first connection terminals 104 connected to the signal cable and the second connection terminals 106 at both ends. In a region where the first connection terminals 104 are formed, the ground terminal 108 is provided.

The shape of the joining member 76 in an extended state is different from that of the second embodiment. In this embodiment, the joining member 76 is formed so that a region where the first connection terminals 104 are formed is formed wider than a region where the second connection terminals 106 are formed. The both end portions of the joining member 76 are substantially straight, which is different from the second embodiment having an arc end portion. By widening the region where the first connection terminals 104 are formed, the interval (pitch) between the first connection terminals 104 can be made wider than the interval (pitch) between the second connection terminals 106. The interval between the first connection terminals 104 can be further widened. The soldering work of the cable core 78 and the joining member 76 can be carried out more easily.

In the joining member 76, the key groove 122 for positioning is formed by cutting out a part of the insulating film 100. Also, by forming the ground pattern 102b on the entire face where the wiring pattern 102a of the insulating film 100 is not formed, a measure against noise is taken. Similarly to the first embodiment, if the joining member 76 is in the laminate structure, the noise measure can be realized by forming the full-face ground pattern, mesh ground or the like at an intermediate position.

Figure 11B:
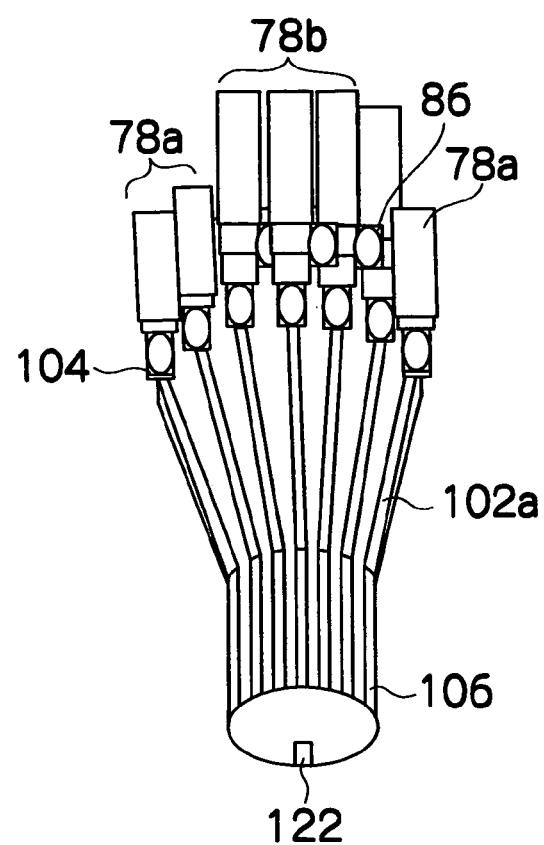

As shown in FIG. 11B, to the first connection terminal 104, the coaxial cable 78a and the single-wire cable 78b are electrically connected. Similarly to the first embodiment, the braided shield 86 is electrically connected to the ground terminal 108. Since the interval between the first connection terminals 104 is formed wide, the soldering work can be carried out easily.

After the connection between the cable core 78 of the signal cable and the first connection terminal 104 is completed, a conduction test is carried out by resistance measurement to check presence of connection failure. In the case of no connection failure, as shown in FIG. 11B, the insulating film 100 is bent by a jig and the like so as to form the joining member 76 having a truncated conical portion to be electrically connected to the cable core 78 and a cylindrical portion to be electrically connected to the connection portion.

In this embodiment, by using the flexible joining member 76, the shape of the joining member is determined after completion of the soldering work. As a result, at a stage where the shape of the joining member is determined, the connection terminals can be arranged so that soldering becomes easy, and the joining member with a small diameter can be obtained by the subsequent molding.

Figure 12A:
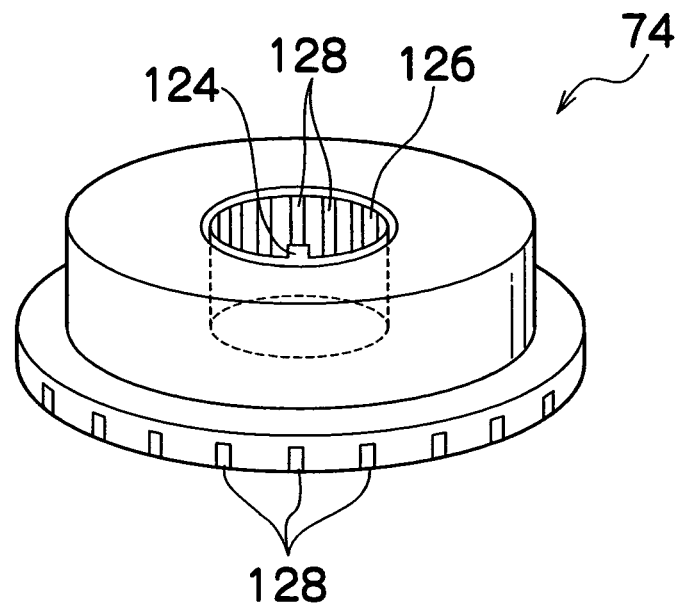
FIGS. 12A and 12B are diagrams for explaining a connection portion according to the third embodiment.

Next, the connection portion 74 to be electrically connected to the joining member 76 of the third embodiment will be described referring to FIGS. 12A and 12B. As shown in FIG. 12A, the connection portion 74 is made of resin or ceramic and has an outer shape of double-stage cylinder. The cylindrical through hole 126 is formed in a vertical direction of the connection portion 74. On the inner face of the through hole 126, the electrode pattern 128 is formed at a position corresponding to a second electrode terminal of the joining member. The electrode pattern 128 is formed by applying gold plating on a copper foil. Also, on the tapered face, the projection portion 124 is formed at a position corresponding to the key groove of the joining member.

Figure 12B:
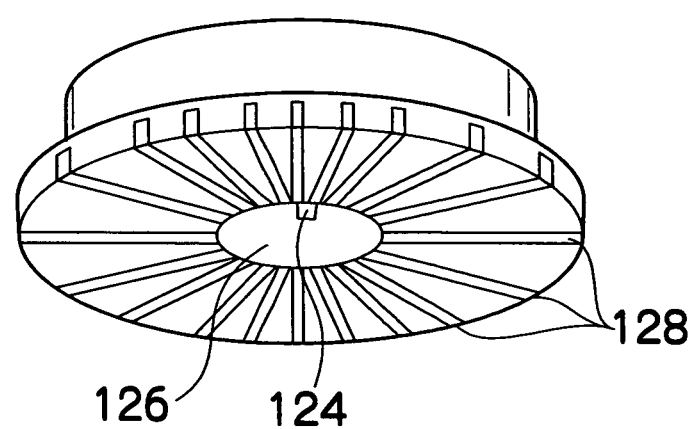

As shown in FIG. 12B, the electrode pattern 128 formed on the inner face of the through hole 126 is extended radially from the through hole 126 on the back face side of the connection portion 74 till it reaches the periphery. The back face of the connection portion 74 becomes a connection surface with the circuit board. Connection between the connection portion 74 and the circuit board is realized through the electrode pattern 128 of the connection portion 74 or ACF, bump and the like formed on the pattern of the circuit board. Since the electrode pattern 128 of the connection portion 74 is formed radially from the center, the interval between the electrode patterns 128 is formed widely on the peripheral portion, and the connection portion 74 and the circuit board are electrically connected relatively easily.

Figure 13:
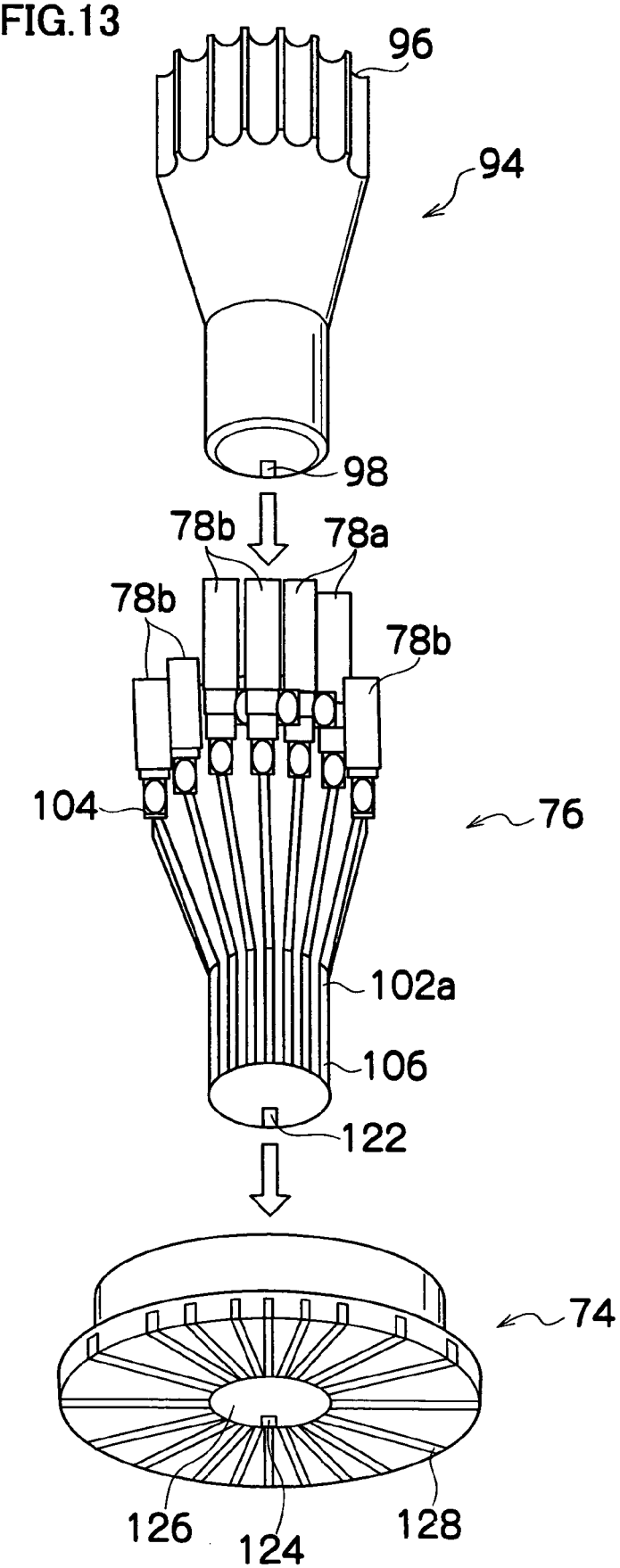
FIG. 13 is a diagram for explaining connection between the joining member and the connection portion according to the third embodiment.

FIG. 13 shows an outline of a method of connecting the joining member 76 and the connection portion 74. Since the shape of a distal end of the joining member 76 and the shape of the through hole 126 of the connection portion 74 are both cylindrical and substantially similar, the joining member 76 is easily inserted into the through hole 126 of the connection portion 74.

At the insertion, the key groove 122 of the joining member 76 is fitted with the projection portion 124 of the connection portion 74, and the electrode pattern 128 of the connection portion 74 and the second connection terminal 106 of the joining member 76 are positioned. By using the fitting between the key groove 122 and the projection portion 124, wrong connection between the electrode pattern 128 and the second connection terminal 106 can be prevented.

In order to further ensure connection between the electrode pattern 128 and the second connection terminal 106, the pressing member 94 is inserted to be fitted with the joining member 76 from the side opposite the connection portion 74 with respect to the joining member 76. The distal end of the pressing member 94 is cylindrical and has a shape substantially similar to the shapes of the joining member 76 and the through hole 126 of the connection portion 74.

By forming a sandwich structure in which the joining member 76 is sandwiched by the pressing member 94 and the connection portion 74, the electrode pattern 128 and the second connection terminal 106 can be electrically connected not particularly using solder and the like, and the joining member 76 and the connection portion 74 are constructed in a detachable structure. With this structure, time for failure analysis and repair can be reduced.

In the pressing member 94, the support groove 96 accommodating cable cores 78 (78*a*, 78*b*) and the key groove 98 for positioning are formed.

Assembling is carried out such that 1) the key groove 122 and the projection portion 124 are fitted together and while the joining member 76 and the connection portion 74 are aligned, the joining member 76 is inserted into the connection portion 74; 2) the key groove 98 of the pressing member 94 and the projection portion 124 are fitted together and while the pressing member 94 and the connection portion 74 are aligned, the pressing member 94 is accurately inserted into the joining member 76; 3) the cable core 78 is bonded and fixed to the support groove 96 formed on the pressing member 94; and 4) the connection portion 74 is mounted on the circuit board. However, the order is not limited to the above.

In the third embodiment, since the joining member 76 has a cylindrical shape at its distal end unlike the second embodiment, connection reliability can be improved. That is, since the joining member 76 realizes electrical connection by being fitted in the through hole 126 of the connection portion 74, even if there is slight displacement in a positional relation between the joining member 76 and the connection portion 74, electrical connection can be maintained.

According to the present invention, in the image pickup device for endoscope, the joining work can be made more efficient and simplified and maintenance performance can be also improved. Also, the size and diameter of the endoscope image pickup device can be reduced.

Input/output signals can be stabilized (noise reduction). Application range is widened such as integration with peripheral circuit boards, which can further contribute to the reduction of size and diameter of the endoscope image pickup device.

By using the connection portion, electric performance tests can be carried out only for the solid-state image pickup element and the peripheral circuit board. Instead of conventional comprehensive inspection by connecting the signal cable, inspection of a single piece is made possible by mounting a common connector to an inspecting device, and process certification can be segmented, which contributes to quality stabilization. Also, time for failure analysis and repair can be reduced.

The invention claimed is:

1. An image pickup device, comprising:
 a solid-state image pickup element;
 a circuit board electrically connected to the solid-state image pickup element;
 a signal cable having a plurality of cable cores supplying power and a driving signal to the solid-state image pickup element; and
 a joining member having a wiring pattern electrically connecting the signal cable and the circuit board, wherein
 the joining member has a plurality of first connection terminals connected to the cable cores of the signal cable and a plurality of second connection terminals connected to the circuit board at both ends of the wiring pattern, and the interval between the first connection terminals is wider than the interval between the second connection terminals; wherein the joining member is formed cylindrically so that a length of an end portion where the first connection terminals are formed is longer than a length of an end portion where the second connection terminals are formed, and an outer diameter on the side connected to the signal cable is larger than an outer diameter on the side connected to the circuit board.

2. The image pickup device according to claim 1, wherein the joining member is a flexible member in which a wiring pattern is formed on an insulating film.

3. The image pickup device according to claim 1, further comprising: a connection portion between the circuit board and the joining member, and wherein the circuit board and the joining member are electrically connected through the connection portion.

4. The image pickup device according to claim 3, wherein the joining member and the connection portion are positioned and fixed by engagement between a groove or a projection formed on the joining member and a projection or a groove formed on the connection portion.

5. The image pickup device according to claim 3, wherein the joining member and the connection portion are provided detachably.

6. The image pickup device according to claim 1, further comprising: a pressing member arranged on the side opposite to the connection portion with respect to the joining member, and wherein the joining member is sandwiched between the joining member and the pressing member.

7. The image pickup device according to claim 1, wherein the joining member is provided with a full-face ground pattern or mesh ground pattern on a face where the wiring pattern is not formed.

8. The image pickup device according to claim 1, wherein the joining member is in a laminate structure in which a plurality of conductor patterns and insulating films are laminated, and the conductor pattern located in the middle is made the full-face ground pattern or mesh ground pattern.

9. An endoscope comprising the image pickup device according to claim 1.

10. The image pickup device according to claim 1, wherein the joining member is a flexible member in which a wiring pattern is formed on an insulating film.

11. The image pickup device according to claim 10, further comprising: a connection portion between the circuit board and the joining member, and wherein the circuit board and the joining member are electrically connected through the connection portion.

12. The image pickup device according to claim 11, wherein the joining member and the connection portion are positioned and fixed by engagement between a groove or a projection formed on the joining member and a projection or a groove formed on the connection portion.

13. The image pickup device according to claim 12, wherein the joining member and the connection portion are provided detachably.

14. The image pickup device according to claim 13, further comprising: a pressing member arranged on the side opposite to the connection portion with respect to the joining member, and wherein the joining member is sandwiched between the joining member and the pressing member.

15. The image pickup device according to claim 14, wherein the joining member is provided with a full-face ground pattern or mesh ground pattern on a face where the wiring pattern is not formed.

16. The image pickup device according to claim 15, wherein the joining member is in a laminate structure in which a plurality of conductor patterns and insulating films are laminated, and the conductor pattern located in the middle is made the full-face ground pattern or mesh ground pattern.

17. An endoscope comprising the image pickup device according to claim 16.

* * * * *